(12) United States Patent
Baumoel (10) Patent No.: US 10,473,502 B2
(45) Date of Patent: Nov. 12, 2019

(54) DIELECTRIC MULTIPHASE FLOW METER

(71) Applicant: Joseph Baumoel, Wellington, FL (US)

(72) Inventor: Joseph Baumoel, Wellington, FL (US)

( * ) Notice: Subject to any disclaimer, the term of this patent is extended or adjusted under 35 U.S.C. 154(b) by 0 days.

(21) Appl. No.: 16/290,068

(22) Filed: Mar. 1, 2019

(65) Prior Publication Data

US 2019/0277680 A1 Sep. 12, 2019

Related U.S. Application Data

(60) Provisional application No. 62/636,898, filed on Mar. 1, 2018.

(51) Int. Cl.
| | |
|---|---|
| *G01F 1/712* | (2006.01) |
| *G01N 27/02* | (2006.01) |
| *G01F 1/74* | (2006.01) |
| *G01N 29/22* | (2006.01) |
| *G01F 1/66* | (2006.01) |
| *G01N 27/22* | (2006.01) |

(52) U.S. Cl.
CPC .............. *G01F 1/74* (2013.01); *G01F 1/66* (2013.01); *G01F 1/712* (2013.01); *G01N 27/026* (2013.01); *G01N 27/221* (2013.01); *G01N 29/222* (2013.01); *G01N 2291/02433* (2013.01); *G01N 2291/02836* (2013.01)

(58) Field of Classification Search
CPC ..... G01F 1/712; G01N 27/026; G01N 27/221
See application file for complete search history.

(56) References Cited

U.S. PATENT DOCUMENTS

| | | | |
|---|---|---|---|
| 4,397,190 A | 8/1983 | Hulin | |
| 4,841,780 A | 6/1989 | Inada et al. | |
| 4,882,928 A | 11/1989 | Lane, Jr. et al. | |
| 5,929,342 A | 7/1999 | Thompson | |
| 6,272,915 B1 * | 8/2001 | Kostelnicek | E21B 47/042 |
| | | | 73/152.28 |
| 6,405,603 B1 | 6/2002 | Baumoel | |
| 6,587,796 B2 | 7/2003 | Fukuhara | |
| 6,655,221 B1 * | 12/2003 | Aspelund | G01F 1/363 |
| | | | 73/861.04 |
| 8,694,270 B2 | 4/2014 | Huang et al. | |
| 9,052,230 B2 | 6/2015 | Kutlik et al. | |
| 9,625,305 B2 | 4/2017 | Schaefer et al. | |
| 9,746,360 B2 | 8/2017 | DeSilva et al. | |
| 9,880,133 B1 | 1/2018 | Stephanou | |
| 2002/0134140 A1 | 9/2002 | Baumoel | |
| 2003/0203500 A1 * | 10/2003 | Carlson | G01N 27/221 |
| | | | 506/7 |

(Continued)

*Primary Examiner* — Herbert K Roberts
(74) *Attorney, Agent, or Firm* — F. Chau & Associates, LLC (57) ABSTRACT

A sensor is provided for detecting relative amounts of components within a mixture. The sensor includes a dielectric transducer comprising a first conductive rod and a second conductive rod; an oscillator configured to apply a voltage to the first conductive rod; an amplifier configured receive a voltage from the second conductive rod as input; and a controller configured to periodically sample an output voltage of the amplifier to generate a plurality of sample voltages, compare the sample voltages against distinct voltage values for identifying each of the components to determine the relative amounts of the components.

18 Claims, 8 Drawing Sheets

(56) References Cited

U.S. PATENT DOCUMENTS

| | | |
|---|---|---|
| 2005/0264302 A1 * | 12/2005 | Mohajer .............. G01N 22/00 324/639 |
| 2008/0163700 A1 | 7/2008 | Huang |
| 2010/0251829 A1 | 10/2010 | Davis |
| 2010/0299068 A1 | 11/2010 | Huang et al. |
| 2013/0167655 A1 | 7/2013 | Fujii et al. |
| 2015/0160052 A1 | 6/2015 | Wiest et al. |

* cited by examiner

| % Gas | % Oil in Water Mixture >>> | | | | | | | | | | |
|---|---|---|---|---|---|---|---|---|---|---|---|
| | Dielectric Constant | | | | | | | | | | |
| | 0 | 10 | 20 | 30 | 40 | 50 | 60 | 70 | 80 | 90 | 100 |
| 0 | 80.0 | 71.8 | 65.0 | 59.2 | 54.0 | 49.3 | 45.0 | 41.0 | 37.1 | 33.5 | 30.0 |
| 10 | 40.5 | 36.8 | 33.7 | 31.0 | 28.6 | 26.5 | 24.5 | 22.6 | 20.8 | 19.1 | 17.4 |
| 20 | 34.5 | 31.2 | 28.5 | 26.1 | 24.0 | 22.1 | 20.4 | 18.8 | 17.2 | 15.7 | 14.3 |
| 30 | 29.8 | 26.9 | 24.5 | 22.5 | 20.6 | 19.0 | 17.5 | 16.1 | 14.7 | 13.4 | 12.2 |
| 40 | 25.4 | 23.0 | 20.9 | 19.2 | 17.6 | 16.2 | 14.9 | 13.7 | 12.5 | 11.4 | 10.4 |
| 50 | 21.2 | 19.2 | 17.5 | 16.0 | 14.7 | 13.6 | 12.5 | 11.5 | 10.5 | 9.6 | 8.7 |
| 60 | 17.1 | 15.5 | 14.1 | 13.0 | 11.9 | 11.0 | 10.1 | 9.3 | 8.5 | 7.8 | 7.1 |
| 70 | 13.1 | 11.8 | 10.8 | 9.9 | 9.2 | 8.5 | 7.8 | 7.2 | 6.6 | 6.1 | 5.6 |
| 80 | 9.0 | 8.2 | 7.5 | 6.9 | 6.4 | 6.0 | 5.5 | 5.1 | 4.7 | 4.4 | 4.0 |
| 90 | 5.0 | 4.6 | 4.3 | 4.0 | 3.7 | 3.5 | 3.3 | 3.1 | 2.9 | 2.7 | 2.5 |
| 100 | 1 | 1 | 1 | 1 | 1 | 1 | 1 | 1 | 1 | 1 | 1 |

| E | R | V | Kx | "/M |
|---|---|---|---|---|
| 8.85E-12 | 0.1875 | 45 | 1 | 0.0254 |

C=Sum(0—H)EK(dH)wh/t

| %R=r | r=h=t | Theta | Cos Theta | w | t | dC | C as f(V%) |
|---|---|---|---|---|---|---|---|
| 0 | 0.00 | 0.0 | 1.00 | 0.38 | 0 | #DIV/0! | 0 |
| 0.1 | 0.02 | 5.7 | 0.99 | 0.37 | 0.0375 | 2.24E-12 | 2.24E-12 |
| 0.1 | 0.04 | 11.5 | 0.98 | 0.37 | 0.075 | 1.1E-12 | 3.34E-12 |
| 0.1 | 0.06 | 17.5 | 0.95 | 0.36 | 0.1125 | 7.15E-13 | 4.05E-12 |
| 0.1 | 0.08 | 23.6 | 0.92 | 0.34 | 0.15 | 5.15E-13 | 4.57E-12 |
| 0.1 | 0.09 | 30.0 | 0.87 | 0.32 | 0.1875 | 3.9E-13 | 4.96E-12 |
| 0.1 | 0.11 | 36.9 | 0.80 | 0.30 | 0.225 | 3E-13 | 5.26E-12 |
| 0.1 | 0.13 | 44.4 | 0.71 | 0.27 | 0.2625 | 2.29E-13 | 5.49E-12 |
| 0.1 | 0.15 | 53.1 | 0.60 | 0.23 | 0.3 | 1.69E-13 | 5.66E-12 |
| 0.1 | 0.17 | 64.2 | 0.44 | 0.16 | 0.3375 | 1.09E-13 | 5.77E-12 |
| 0.1 | 0.19 | 90.0 | 0.00 | 0.00 | 0.375 | 1.38E-29 | 5.77E-12 |

DIELECTRIC MULTIPHASE FLOW METER

CROSS-REFERENCE TO RELATED APPLICATIONS

This application claims priority to U.S. Provisional Application No. 62/636,898, filed on Mar. 1, 2018 the disclosure of which is incorporated by reference herein.

TECHNICAL FIELD

The present disclosure relates to a flow meter, and more particularly to a dielectric multiphase flow meter.

DISCUSSION OF RELATED ART

Industrial processes frequently involve measuring the content of a mixed medium. For example, these processes involve determining how much of each component contributes to the mixture itself. And, in some cases, it is necessary to determine the flow rate of the mixture, either to control a processing operation, or to determine the rate of flow for commercial or operational purposes.

Exemplary of this need is in the production of oil. A well is sunk in the hope that it reaches a location from which large quantities of crude can be extracted. However, since crude oil is frequently a mixture of Oil, Gas and Water, plus sand, it's non-descript nature makes it difficult to determine the relative percentage of each component, and even more difficult to determine the flow rate from each well. Accordingly, it is desired to provide a means of measuring these parameters at each well-head, in an accurate and cost-effective way.

Various means have been devised to accomplish this objective, with varying degrees of success, and at relatively high cost, using devices which employ multiple measuring techniques. It is desired to develop a modestly priced "single technology" device which promises excellent accuracy in determining the relative amount of each component, and an accurate measure of flow rate.

SUMMARY OF THE INVENTION

Embodiments of the inventive concept include a dielectric multiphase flowmeter that provides excellent accuracy in determining the relative amount of each component in a mixed medium, and an accurate measure of the flow rate of the medium.

At least one embodiment of the inventive concept provides a capacitive Transducer utilizing ground shielded metal electrodes shaped to constrict the electrical field pattern to a small region of space relative to its physical dimensions to enhance its resolution for determining the dielectric constant and electrical impedance of liquids or gases in small regions of space, such as a bubble.

At least one embodiment of the inventive concept provides a means of determining the relative volumes of the Phases of Oil, Gas and Water flowing in a pipe or container, by measuring the differing electrical impedance of these Phases as they pass through the sensitive field region of the Multiphase Transducer, and by integrating the time durations of each detected Phase Signature.

At least one embodiment of the inventive concept provides a means of memorizing the impedance and phase angle "Signature" of the material currently in the field of the Transducer and using this data in the process of determining the Phase of that material, as between bubbles of Oil, Gas or Water.

At least one embodiment of the inventive concept provides a means of measuring the flow rate of a Medium flowing in a pipe by detecting and recording a medium's Phase related electrical impedance and phase shift Signatures, as it flows sequentially past each of two Multiphase Transducers, located a known distance d from each other within a pipe, and by correlating the time sequence of the recorded data generated by each of the Transducers to determine the time t taken for the Medium to travel that distance, permitting the computation of the flow velocity v (i.e. d/t=V).

At least one embodiment of the inventive concept provides a means of confining Medium flow in the region between the upstream Reference and downstream Correlation Multiphase Transducers to minimize Phase Mixing, so as to enhance Correlation effectiveness.

At least one embodiment of the inventive concept provides a means of measuring the current flowing through a Multiphase Transducer and converting it to a proportional voltage capable of being digitized and memorized in a register, and a FIFO to permit correlation.

At least one embodiment of the inventive concept provides A means of direct connection of a Multiphase Transducer to a personal computer (PC) board located within an integral Multiphase Flow Computer.

According to an exemplary embodiment of the inventive concept, a sensor for detecting relative amounts of components within a mixture is provided. The sensor comprises a dielectric transducer having a first conductive rod and a second conductive rod; an oscillator configured to apply a voltage to the first conductive rod; an amplifier configured receive a voltage from the second conductive rod as input; and a controller configured to periodically sample an output voltage of the amplifier to generate a plurality of sample voltages, compare the sample voltages against distinct voltage values for identifying each of the components to determine the relative amounts of the components.

In an embodiment, the controller determines the relative amounts of the components by integrating the relative amount of time each component was identified.

In an embodiment, the first conductive rod includes a first angled front side disposed at a first acute angle relative to a first back side of the first conductive rod, the second conductive rod includes a second angled front side disposed at a second angle relative to a second back side of the second conductive rod, the first and second angled front sides face each other, and the mixture flows through a space between the first and second front angled sides.

In an embodiment, the first conductive rod includes a first portion below the first angled side and a second portion below the second angled side, and the dielectric transducer includes a three-layer region between the first and second portions, the three-layer region including a first insulator covering a first side of the first portion, a second insulator covering a second side of the second portion, and a conductive sheet between the insulators that is grounded.

In an embodiment, the first and second sides are flat and the back sides are semi-conical.

In an embodiment, the amplifier is designed so that its output voltage is a first voltage value among the distinct voltage values to indicate Oil, a second voltage value among the distinct voltage values to indicate Gas, and a third voltage value among the distinct voltage values to indicate Water.

In an embodiment, the sensor further includes a phase comparator configured to operate on a voltage applied by the oscillator and an output voltage of the amplifier to determine a phase difference, wherein the controller uses both the output voltage and the phase difference to determine a given one of the components of the mixture.

In an embodiment, the controller determines the given one component is Oil when the output voltage is a first voltage value among the distinct voltage values and the phase difference is 90 degrees, the controller determines the given one component is a mixture of Water and Gas when the output voltage is the first voltage value and the phase difference is less than 90 degrees.

In an embodiment, the controller determines the given one component is Gas when the output voltage is a second voltage value among the distinct voltage values and the phase difference is less than 90 degrees, the controller determines the given one component is a mixture of Water and Oil when the output voltage is the second voltage value and the phase difference is less than 90 degrees.

In an embodiment, the controller determines the given one component is Water when the output voltage is a third voltage value among the distinct voltage values.

In an embodiment, the sensor further includes a variable capacitor connected to the input of the amplifier, wherein the voltage applied by the oscillator to the first conductive rod has a positive polarity, and the oscillator applies the voltage of a negative polarity to the variable capacitor.

According to an exemplary embodiment of the inventive concept, dielectric flowmeter is provided. The flowmeter includes a first dielectric transducer comprising a first pair of conductive rods, a first oscillator configured to apply a first voltage to a first conductive rod of the first pair, a first amplifier configured receive a voltage from a second conductive rod of the first pair as an input; a second dielectric transducer comprising a second pair of conductive rods, a second oscillator configured to apply a second voltage to a first conductive rod of the second pair, a second amplifier configured receive a voltage from a second conductive rod of the second pair as an input; and a controller configured to determine a flow rate from an output of the first amplifier and an output of the second amplifier.

In an embodiment, the flowmeter further includes a spool, wherein the first pair of conductive rods is inserted into an interior of the spool at a first position, and the second pair of conductive rods is inserted into the interior at a second position.

In an embodiment, the spool includes a hollow tube (e.g., a flow conditioner), and each of the conductive rods are further inserted into the tube.

In an embodiment, each conductive rod includes an angled front side disposed at an acute angle relative to a back side of the corresponding conductive rod.

In an embodiment, each pair of conductive rods includes a three-layer region between the corresponding conductive rods, the three-layer region including a first insulator covering a first side of a rod of the corresponding pair, a second insulator covering a second side of the other rod of the corresponding pair, and a conductive sheet between the insulators that is grounded.

In an embodiment, each amplifier is designed so that its output voltage is a first voltage value to indicate Oil, a second voltage value to indicate Gas, and a third voltage value to indicate Water, wherein the voltage values differ from one another.

In an embodiment, the first dielectric transducer includes a first buffer storing first values generated from outputs of the first amplifier, and the second dielectric transducer includes a second buffer storing second values generated from outputs of the second amplifier.

In an embodiment, the controller generates a first pattern from the first values, generates a second pattern from the second values, and determines the flow rate when the first pattern is similar to the second pattern by subtracting a time the second pattern is detected from a time the first pattern is detected to generate a travel time and dividing a distance between the positions by the travel time.

In an embodiment, the first dielectric transducer filters out outputs of the first amplifier having a certain phase difference with the first voltage, the second dielectric transducer filters out outputs of the second amplifier having the certain phase difference with the second voltage, and the controller determines the flow rate from the remaining outputs of the first amplifier and from the remaining outputs of the second amplifier.

BRIEF DESCRIPTION OF THE DRAWINGS

Exemplary embodiments of the invention can be understood in more detail from the following descriptions taken in conjunction with the accompanying drawings in which.

DETAILED DESCRIPTION

Exemplary embodiments of the present invention will be described below in more detail with reference to the accompanying drawings. This invention may, however, be embodied in different forms and should not be construed as limited to the embodiments set forth herein. Rather, these embodiments are provided so that this disclosure will be thorough and complete, and will fully convey the scope of the invention to those skilled in the art.

Embodiments of the inventive concept include a dielectric multiphase flowmeter that provides excellent accuracy in determining the relative amount of each component in a mixed medium, and an accurate measure of a flow rate of the medium. Embodiments of the dielectric multiphase flowmeter described below, offer a "single technology" solution, which though intrusive, promises a robust and low-cost solution.

A dielectric multiphase flowmeter is charged with measuring the flow rate of hydrocarbon products, (or other mixed components), under chaotic conditions where the components of the flowing medium are of indeterminate type, relative quantity and distribution. In addition to flow rate, it is usually desired to also determine the types, relative quantity and physical distribution of the components.

Typical of the applications of a Multiphase flowmeter is its use in the Oil and Gas industry, especially at the wellhead or pipeline distribution system, where the data may have use in maximizing production or distribution of crude oil, which may include various percentages of free gas. Applications also exist in general industrial chemical and related processing, not always requiring measurement of flow rate.

To determine the relative amount of Oil, Gas and Water in a mixture it is necessary to identify some common property of each which is sufficiently different from each other, and which is measurable by the same technology. And, since the components are mixed in random ways, it is necessary that the flow measuring technology not be influenced by either the relative amount of each component, nor by the physical distribution of each in the mixture, to a degree which precludes satisfactory accuracy.

A candidate for such a measuring technology is the difference in the relative permittivity of each component. The relative permittivity of a material is its (absolute) permittivity expressed as a ratio relative to the permittivity of a vacuum. Permittivity is a material property that affects the Column force between two point charges in the material. Relative permittivity is the factor by which the electric field between the charges is decreased relative to a vacuum. Likewise, relatively permittivity is the ratio of the capacitance of a capacitor using that material as a dielectric, compared with a similar capacitor that has a vacuum as its dielectric. Relative permittivity is also commonly known as a dielectric constant K. For example, as an approximation. K=1 for gas (e.g., natural gas), K=2 for oil, and K=80 for water, which are sufficiently different to anticipate the ability to differentiate the degree to which each component contributes to the net capacitance of a suitably configured dielectric sensing means (transducer) located within a crude oil flow stream at a wellhead. In addition, the presence of water contaminated by conductive materials, such as salt, will effectively alter the sensed electrical parameters, such as signal phase angle, of the mixture in such a way as to be identified and in some ways quantified.

It should be noted that Oil and Water do not combine uniformly, unless in the form of an emulsion. In such a case, a long settling time would be required for the components to separate without special treatment. Accordingly, these two components (e.g., Oil and Water) typically exist in the form of mixtures of varying sized bubbles, rather than as emulsions. Further, depending on the size of these bubbles relative to the volumetric resolution of the dielectric sensing transducer, these bubbles may or may not be detected according to their individual nature. If components exist as distinct bubbles, and mostly fill the sensing region of the transducer, the ability to determine the relative amount of each will be enhanced so long as the resolution of the transducer is higher (i.e., smaller) than the size of the bubbles.

Figure 1A:
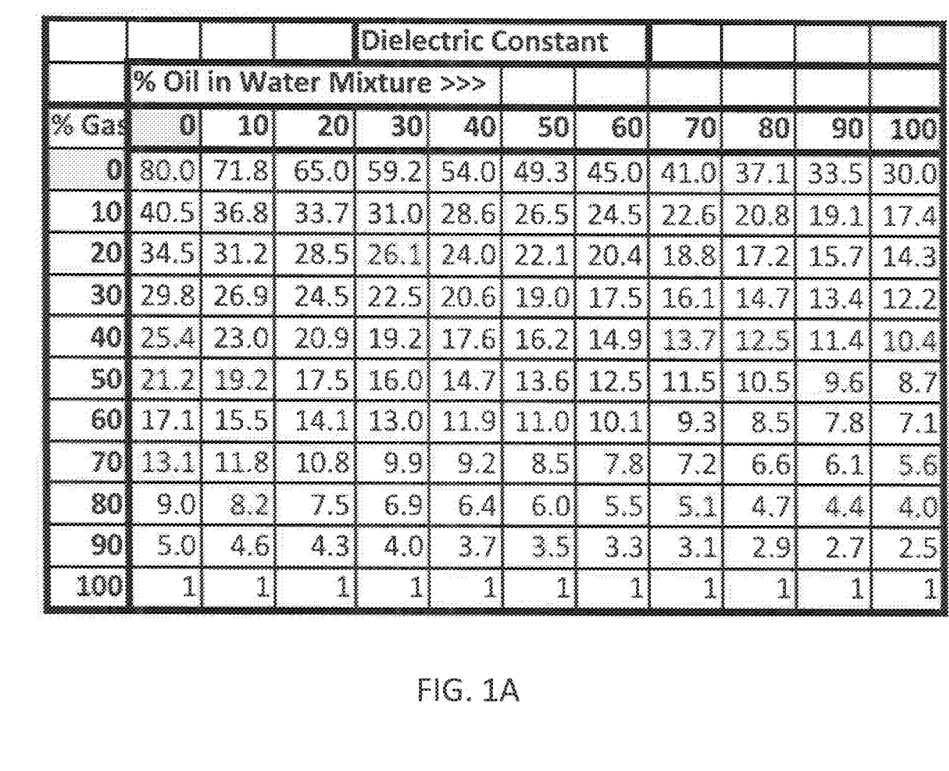
FIG. 1A shows exemplary dielectric constants that are representative of percentages of Oil and Gas.

Note that a transducer that does "bulk" measurement, instead of small volume "bubble" sized resolution would be faced with the problem of determination of what combination of phases would be present that underlay the current measurement. The study shown in FIG. 1A shows that such a bulk signature is not unique, and accordingly it could be difficult, if not impossible, to accurately determine what phases were actually present. In addition, if it is desired to measure not only the phase fractions, but also the flow rate of the medium, it would have its normally random nature averaged, thereby reducing the uniqueness of phase signatures needed for correlation as the medium flows from a reference site to a correlation site downstream. Accordingly, the dielectric multiphase detection system must sense only a small region of the flow stream, smaller than the normal size of the bubbles of each immiscible phase.

In the case of Gas, it is even less likely that an emulsion would form, although gas may diffuse into Oil and Water to some degree. Again, depending on the size of each "bubble" relative to the resolution of the dielectric detection means, determination of the relative amount of Gas will be either more or less accurate. Accordingly, it is preferred to choose a sensing location in which the distribution of bubbles of all of the medium's phases is uniformly distributed. For example, a location in which gas accumulates at the top of a horizontal pipe would not be acceptable, unless a means of "mixing" the Medium upstream of the transducer location to normalize the phase distribution, is provided.

The objective of multiphase metering is the determination of the relative quantity of Oil Gas and Water produced at each individual Wellhead. However, a combination of Water and Gas within the sensing region of the Transducer can simulate the dielectric constant of Oil. As long as the sensing region is smaller than any of the phase bubbles, the presence of any individual phase can be discriminated. However, even in this case, the use of the phase shift in a sensor current due to the inclusion of conductive components, as expected in water, is important in exposing the presence of Water, instead of an erroneous detection of pure Oil, as the combination of Water and Gas in a sensing region might suggest.

Such an ambiguous condition can be exposed since Wellhead water contains ingredients that make the water somewhat "resistive" electrically, which effectively places a resistor in parallel with the capacitive impedance caused by the dielectric constant of water. If the water was pure and were detected only as a capacitor, the electrical phase of the current through the transducer would "lead" the voltage of the Oscillator by 90 degrees. But the presence of a resistive component would reduce this phase shift towards 0 degrees in proportion to its resistive value. Thus, by measuring the phase shift of the output of an amplifier, it is possible to compute the value of this resistance, and thereby distinguish the presence of water, when mixed with gas, simulate the value of pure oil, and by doing so, avoid an erroneous conclusion that the current measurement represented Oil.

Figure 1B:
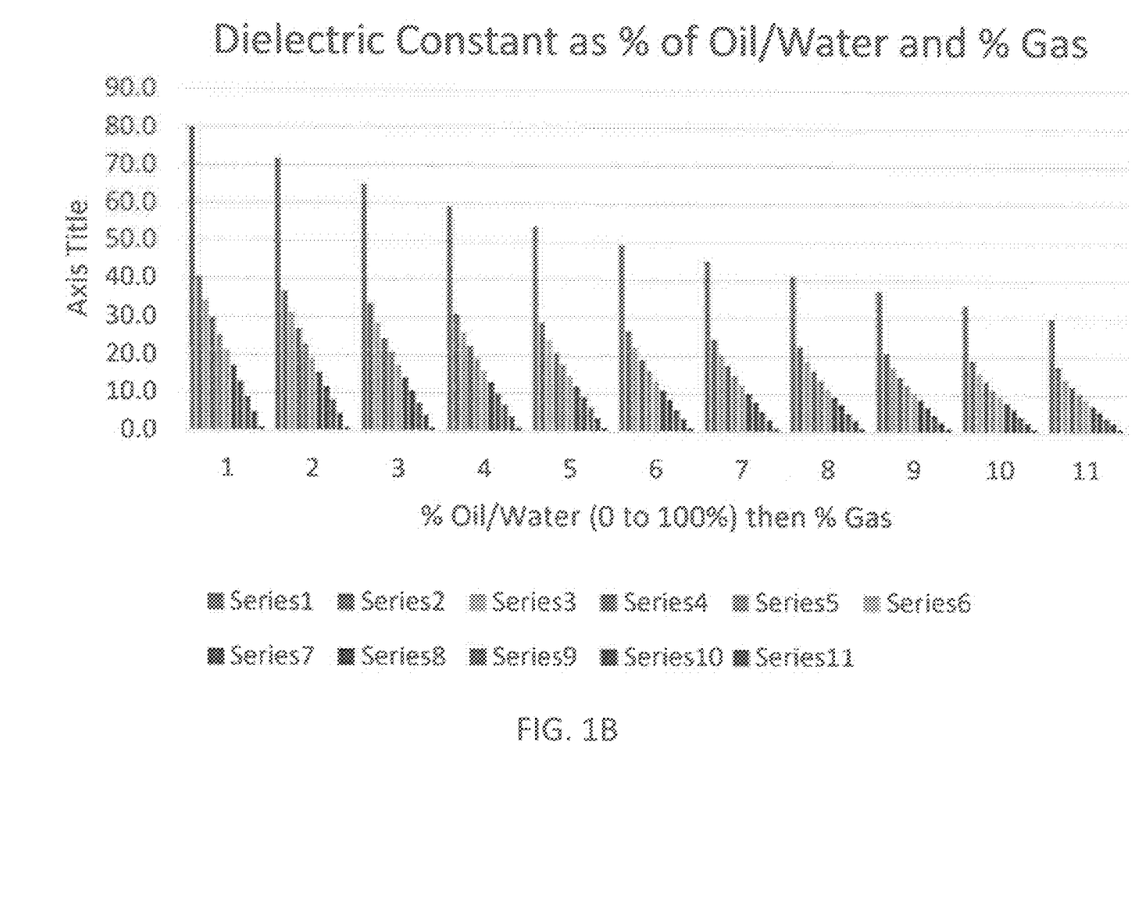
FIG. 1B shows exemplary mixture percentages of Oil in Water and percentages of Gas in Oil/Water mixtures.

To best understand the possible signatures that can be expected (i.e., the resultant electrical impedance of the individual components or a combination of their components), a Dielectric Constant K study has been conducted covering mixture percentages of Oil in Water and percentages of Gas in Oil/Water mixtures, as shown in FIG. 1B.

What is revealed in FIG. 1B (data found in FIG. 1A) is that as the percentage of Oil in Water increases, there is an approximately exponential drop in the perceived mixture's dielectric constant K, from that of Water to that of Oil. And for each such finely divided mixture, relative to the resolution of the dielectric sensor, as the percentage of Gas is increased, the measured dielectric constant K decreases almost linearly to the dielectric constant K of Gas. As noted previously, a bulk measurement of dielectric constant is totally ambiguous, and the conclusion that accurate measurement requires reducing a dielectric transducer to the smallest size possible physically, with the best possible transducer size approaching molecular dimensions, not feasible in practical design.

Fortunately, Oil, Gas and Water are fundamentally immiscible. A transducer of high sensitivity, occupying the smallest space possible, can identify each phase individually so long as the time resolution of detection is fast enough to register before a "bubble" (e.g., a bubble of a first material), then present in the sensor, has started to be replaced by a different phase bubble (e.g., a bubble a second material different from the first). If the medium is flowing, for example, at the rate of 120 inches per second, and a bubble is only ⅛ of an inch in diameter, the current phase in the transducer needs to be detected and digitally registered in less than 1 millisecond. Thus, a transducer operating frequency of at least 1 megahertz (MHz) permits a detection time resolution of 0.1%, which is more than sufficient to permit detecting even such a small bubble, with a resolution of 1% of its size.

Determination of the relative quantity of each component is computed by integrating the relative amount of time each component's "signature" was detected, over a sufficiently long period to establish a consistent average. Such a relative measurement is obtained by generating a "registration" pulse at regular intervals, say every millisecond. Then the current output voltage of the amplifier (e.g., see 405 of FIG. 4) is at a high voltage level, representing the high dielectric constant of Water, or at a medium voltage level, representing Oil, or at a Zero voltage level, representing Gas. This output voltage may be periodically sampled over a period of time to generate a plurality of sample voltages. For example, if a sample voltage is captured every 10 microseconds, and 100 samples are captured, where each sample voltage represents one of Water, Oil, or Gas, then these 10 microsecond time durations can be integrated to determine the relative amounts of Water, Oil, and Gas or a Phase Signature. For example, if 10 of the samples include output voltages representative of Water, 70 of the samples includes output voltages representative of Oil, and 20 of the sample includes output voltages representative of Gas, then it can be concluded that the medium is currently 10% Water, 70% Oil, and 20% Gas. The high frequency AC voltage is constantly demodulated, and then digitized. Whatever its value at the time that a Registration pulse is generated causes one count to be added to either an Oil, Gas or Water register, as determined by a Comparator, which determines the Medium Phase present in the transducer at that time. In fact, intermediate Registers can be provided, for cases where two small bubbles of different Phases occupy the transducer at the same time. Since Oil well production is expected to cover a period of months to years, an averaging period of hours would be acceptable, and would furthermore reveal changes in the relative phase volumes as the well becomes depleted.

To assure that the reported phase quantity relationship is accurate, it is preferred that the transducer be located where the phase bubbles are distributed in relation to their true relative average. What should be avoided is "phase bias" such as a preponderance of Water or Gas different on the average, from the average phase percentages. A location in which, for example, Gas collects at the top of a horizontal pipe, should be avoided. Alternatively, a number of transducers could be distributed at the sensing location so that, in sum, an average measurement can be computed.

Figure 2:
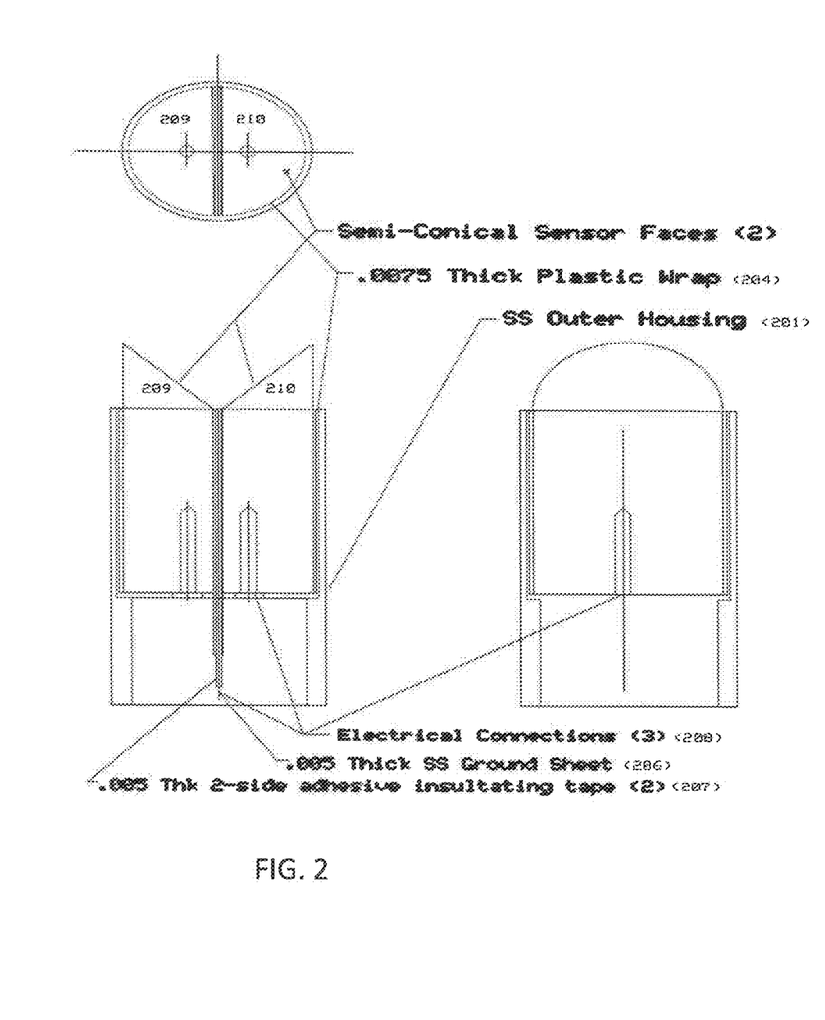
FIG. 2 illustrates a multiphase dielectric transducer according to an exemplary embodiment of the inventive concept.

As noted above, since the components of the stream, Oil, Gas and Water, will frequently remain isolated from each of the other, in the form of small bubbles, it is desired to create a high sensitivity transducer, which occupies the smallest physical space in the flow stream. FIG. 2 shows such a construction, although it is possible to devise alternate embodiments using the same principal.

As shown on FIG. 2, the Multiphase Dielectric Transducer is shaped like a small cylinder, say ⅜ inch in diameter, whose metal exterior "Tube" is intended to be welded inside a hole drilled into a pipe of any size suitable for retrieving Oil at a wellhead. Note that the same principal and physical design can be used for determining relative quantities of any immiscible components in any industrial processing application.

Within the Tube (e.g., outer housing 201) are two metal Rods 209 and 210, each formed from a round metal Rod (e.g., a conductive material like stainless steel). In an embodiment, the round metal Rod ranges from ⅛ to ½ inch in diameter before being axially cut to form Rods 209 and 210. In an embodiment, the Rods 209 and 210 each have a thickness that is less than half a diameter of the original round metal Rod. In an embodiment, one side each of the Rods 209 and 210 is semi-circular, and has a hole 208 drilled into it to accept an electrical connection to the input of the amplifier 405 (e.g., an operational amplifier or OpAmp), shown on FIG. 4.

The other end of each of the Rods 209 and 210 is machined at an angle. For example, an upper portion of each the Rods 209 and 210 are cut at the angle and removed. In an exemplary embodiment, the angle is an acute angle such as 45 degrees. However, embodiments are not limited to 45 degrees since this angle may be increased to support high viscosity applications. The removal of these portions may result in flat surfaces at these angles. In an embodiment, a non-stick surface is adhered to these flat surfaces. In an embodiment, these surfaces are flat to control the capacitance gradient. The two Rods 209 and 210 are positioned so that their flat semi-conical faces face each other, and extend into the interior of the pipe, when installed, so as to be exposed to the Medium which flows through the pipe. Both rods 209 and 210 are enclosed in an insulating tube 201 or shrink wrap which forms a cylinder of approximately the original diameter of the Rod, plus its insulating wrapping, and is placed into the Tube 201 so that it sits on the metal edge on the inside of the Tube 201, near the bottom, which acts to support the Rods 209 and 210 against the high internal pressure of the Wellhead. The Tube 201 may include a plastic wrap 204 surrounding its inner surface to insulate the Rods 209 and 210 from the outer housing 201.

A three-layer region is present between the Rods 209 and 210 in contact with the flat sides. The three layer region includes a ground plate (e.g., Ground Sheet 206), and an insulator 207 (e.g., plastic tape) on opposing sides of the Ground Sheet 206. Thus, the Ground Sheet 206 is surrounded by the insulators 207 so it is electrically insulated from the Rods 209 and 210. In an embodiment, a ground voltage is applied to the Ground Sheet 206. The total diameter of the combination of the Rods 209 and 210, and the three-layer region may the same as the diameter of the original round rod. Each of the Rods 209 and 210 may be considered to have a semi-cylindrical shape.

Since the center Ground Sheet 206 prevents the main body of the Rods 209 and 210 from "seeing" each other dielectrically, the only parts of the Transducer that form a sensing Capacitor are the two semi-conical sections which extend externally into the pipe interior, beyond the Ground Sheet 206. In an embodiment, the Transducer (e.g., a Multiphase Dielectric Transducer) is connected in a circuit that can sense the magnitude of the electrical current, proportional to the differing dielectric constants of the Medium's phases as they pass between the semi-conical exposed faces of the transducer.

This Multiphase Dielectric Transducer enables fast and accurate determination of the relative percentage of each phase by integrating the relative amount of time each phase's bubbles are resident in the Transducer. Other shapes are possible to enhance its sensitivity and sensing dimensions as may be desired for certain applications.

Note that the embodiment shown in FIG. 2 is most sensitive near the bottom of the "V" formed where the semi-conic faces are closest to each other. As we move away from the bottom of the "V", not only is the distance between the faces greater, but the effective width of each face reduces. Accordingly, the effective sensing region of this Transducer embodiment is smaller than the physical size of device itself. This achieves the desired result of a great sensitivity combined with very high bubble size resolution.

Figure 3A:
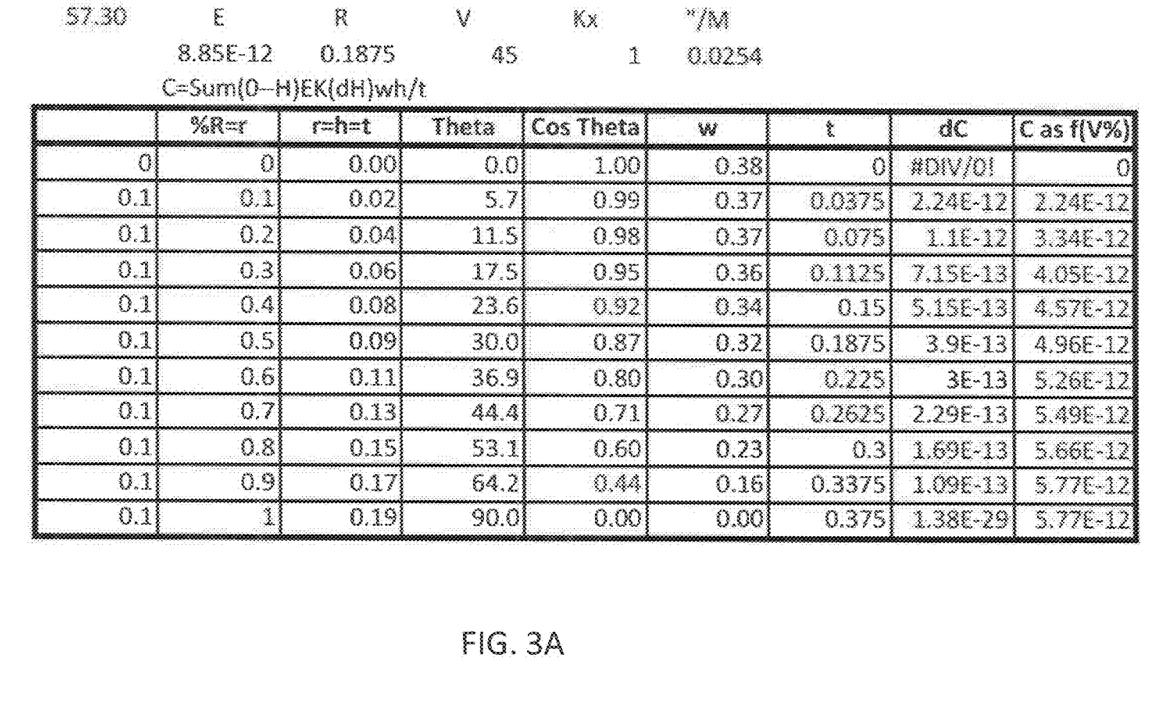
FIG. 3A illustrates computation data of the transducer's relative capacitance gradient.
Figure 3B:
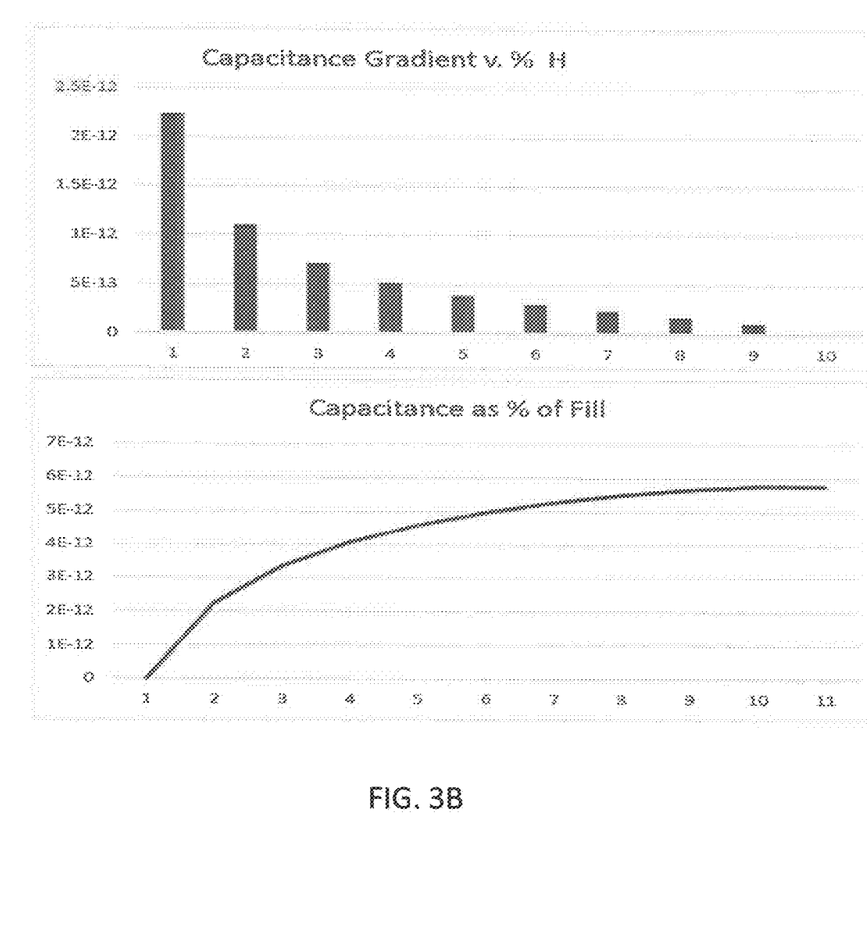
FIG. 3B illustrates where the capacitance gradient is greatest, near the crotch of the transducer's "V"

FIG. 3A shows the computation of the Transducer's relative capacitance gradient for the Transducer design shown in FIG. 2. As shown by FIG. 3B, the capacitance is greatest, as expected, near the bottom of the "V" formed where the conic sections first exit from the Transducer body. In a Transducer of ⅜ inch in diameter, approximately 50% of the total capacitance, around 2 picofarads (pf), is developed in the first 20% (less than 0.04 inches) near the bottom of the "V". A bubble of only 0.1 inch-diameter will produce almost 90% of the Transducer current that would be produced by a bubble of almost twice that size, 0.19 inches. Thus, this Transducer design is extremely sensitive to the small sized bubbles which enable the Dielectric Multiphase Flowmeter, by time integration of each different phase signature to accurately determine the relative percentage of each phase, Gas, Water or Oil.

In practice, the Transducer is oriented so that the Medium flows into the open "V" shape. This will enhance the ability of new "bubbles" to flush out the previously arrived bubble. Depending on the size of each bubble, and the current flow rate, the amount of time spent in transition will be a smaller or greater percentage of the time that each individual Bubble is resident in the sensing region. However, the studies referenced above will permit determining how much of each transition component should be added to the basic Bubble Signature component.

Note that the resolution of the Multiphase transducer is linearly scalable with physical size, having the same capacitance gradient for the same sensor shape, independent of diameter. The benefit of this scalability is that in applications where smaller bubble sizes are expected, simply reducing the physical size will increase the resolution proportionally. This is limited only where the minimum practical dimensions of the Ground Plane preclude proportional size reduction.

Figure 4:
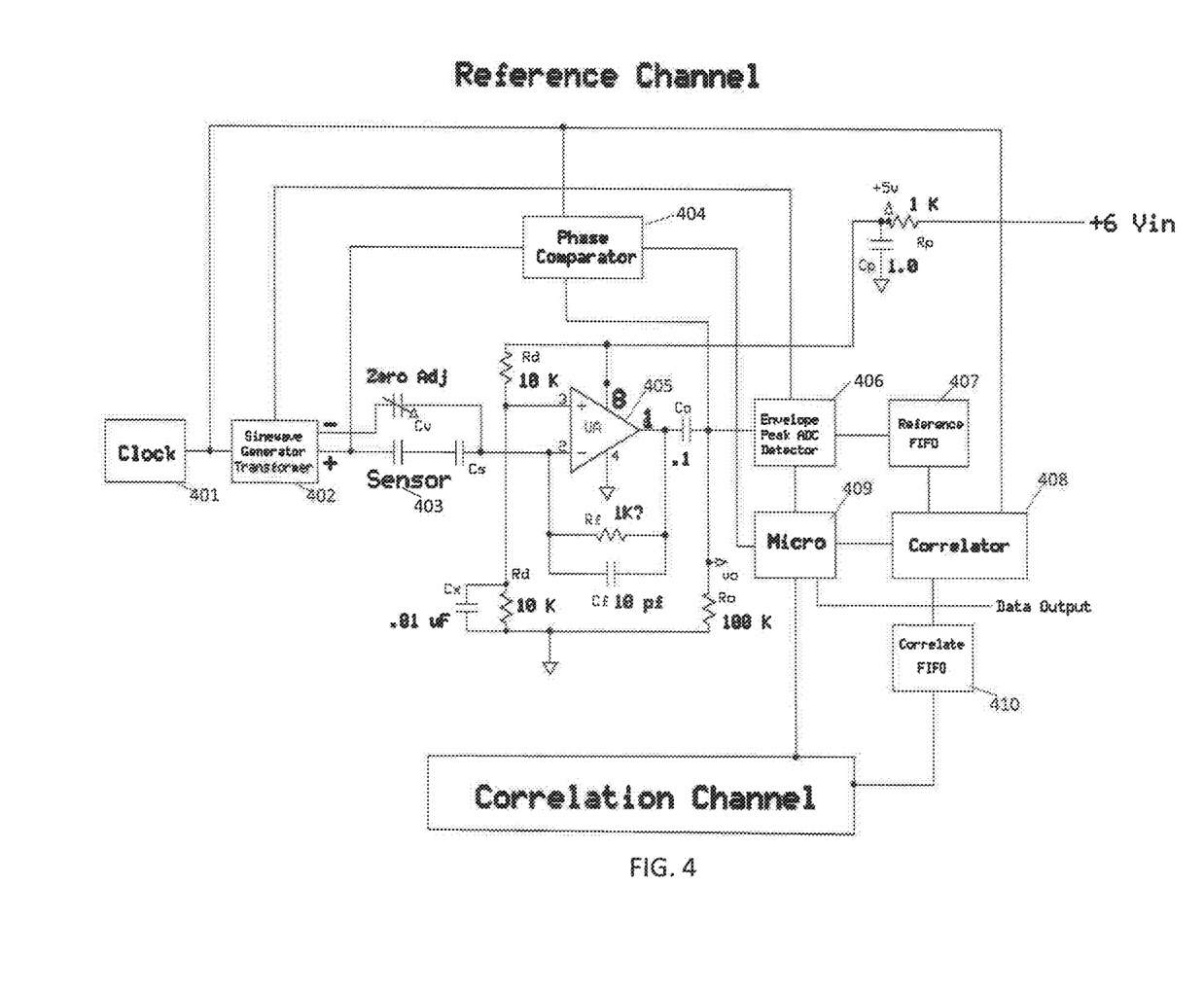
FIG. 4 illustrates a schematic diagram of a flowmeter including the transducer according to an exemplary embodiment of the inventive concept.

FIG. 4 illustrates a Dielectric Multiphase flowmeter including a Dielectric Multiphase transducer of FIG. 2, according to an exemplary embodiment of the inventive concept. The flowmeter includes a clock generator 401, a sine wave synthesizer, together referred to as the Oscillator 402, a sensor 403, a phase comparator 404, an amplifier 405, and envelope peak detector 406, a reference first in first out (FIFO) buffer 407, a correlator 407 (e.g., logic or a logic circuit designed to perform a mathematical correlation of the Phase sequences detected by the Reference transducer against the Correlation transducer sequences), a microprocessor 409, and correlation FIFO buffer 410. A controller may be implemented using one or more of the detector 406, the microprocessor 409, the FIFO 407, and the correlator 408.

In the circuit of FIG. 4, any current which flows through the Transducer (e.g., sensor 403) and the series capacitor Cs enters the negative input terminal of the amplifier 405, which induces feedback current via resistor Rf from the output of the amplifier 405, which exactly balances the Transducer current. If, when the Transducer is filled with only Gas, the capacitor Cv, which is fed from a voltage of opposite polarity from the Oscillator 402, and is adjusted so that its current is equal to that of the Transducer, so that the input current to the negative input terminal of the amplifier 405 will be Zero. Thus, an output voltage of Zero from the amplifier 405 will result, and the Zero output voltage will then indicate that the Transducer is filled with only Gas. In an embodiment, the capacitor Cv is a variable capacitor. In an exemplary embodiment, the capacitance of the capacitor Cv is set during manufacture when connected to the Transducer. At that time, the Transducer is filled with air, which has the same dielectric constant as the Gas in an Oil Well. Since that gas produces current into the Amplifier 405, which is only half the value that would be produced when Oil is present, it uses up some of the "space" needed to distinguish between the presence of Oil or Gas. Since the capacitor Cv feeds a current of opposite phase angle to that of the Transducer, it capacitance value can be adjusted to be equal to the current from the air filled transducer. Accordingly, we are able to identify Gas when the output voltage is Zero volts, rather than half of the Oil value of 0.5 volts, or 0.25 volts, making it much less likely that we could misinterpret Gas as being Oil.

But, when the Transducer is filled with Water, with a dielectric constant of approximately 80, the current will be limited by its capacitance in series with capacitor Cs, and in that case, the value of resistor Rf will have been previously selected so that the output voltage of the amplifier 405 will be, say, 1 volt, signifying that the Transducer is filled with only Water. But when the Transducer is filled with only Oil, of dielectric constant, say, 2 the current into the amplifier 405 will be determined by its capacitance in series with capacitor Cs.

Accordingly, by selecting the capacitance value of capacitor Cs so that when the Transducer is filled with Oil, the current into the negative terminal of the amplifier 405 is such that the output voltage is, say, 0.5 volts. Thus, we have a deterministic identification of what Phase is currently being sensed by the Transducer. For example, in at least one exemplary embodiment, the amplifier 405 outputs 0 volts to indicate Gas, 0.5 volts to indicate Oil, and 1.0 volts to indicate Water. Please note that the inventive is not limited to use of 0 volts, 0.5 volts, and 1.0 volts to indicate Gas, Oil, and Water, respectively. For example, the resistances of the resistors and capacitances of the capacitors in the circuit can be changed so that three other distinct voltages are used to indicate Gas, Oil, and Water, respectively.

Once one of these types of medium is detected, a Registration pulse can be generated to cause a count to be added to a respective Register of FIFO 407. For example, the microcontroller 409 can output the registration pulse to the detector 406 upon detecting a given one of the mediums, and then the detector 406 in response to receiving a rising or falling edge of the registration pulse can increment the count of a corresponding one of the registers of the FIFO 407. The FIFO 407 may also be used to store a certain number of samples (e.g., a history) for a given period, where each sample indicates either the output voltage of the amplifier 405 or a value that indicates the current sample is considered Oil (e.g., a first value), Gas (e.g., a second value different from the first value), or Water (e.g., a third value different from the first and second values).

However, there may be cases where an output voltage of 0.5 volts that should be indicative of Oil in certain embodiments is an error because the medium in the Transducer is actually a combination of Water and Gas, or an output voltage of 0 volts that should be indicative of Gas in certain embodiments is an error because the medium in the Transducer is actually a combination of Oil and Water.

Thus, the phase comparator 404 can be used as a tie-breaker to determine whether 0.5 volts is Oil or a combination of Water and Gas, and whether 0 volts is Gas or a combination of Water and Oil. Thus, when the Registration pulse is triggered, the phase information output by the phase comparator 404 will allow a count to be placed into the proper Phase Count register, which will therefore accumulate counts in proportion to the relative percentage of each phase (e.g., Oil, Gas or Water) which populates the medium. It is also possible to recognize intermediate values of the Phase signature, and establish independent Registers for each which will permit computation of the relative quantity of the Phase bubbles which may simultaneously occupy the sensing region of the Transducer at that time.

For example, the phase comparator 405 can be used to determine whether the output signal of the amplifier 405 is phased at 90 degrees earlier than the current phase of the signal output by the Oscillator 402. For example, the phase comparator 405 can receive an output of the Oscillator 402 (e.g., the positive output terminal) and an output of the amplifier 405 as inputs, and compare the inputs to determine a phase difference, and output the phase difference to the microcontroller 409 or the detector 406.

In an exemplary embodiment, when the phase difference is 90 degrees and the output voltage of the amplifier 405 is the voltage indicative of Oil (e.g., 0.5 volts), it can be concluded that the medium is in fact Oil. However, if the phase difference is less than 90 degrees and the output voltage of the amplifier 405 is the voltage indicative of Oil, it can be concluded that the medium is in fact a combination of Water and Gas. In an exemplary embodiment, when the output of the amplifier 405 is indicative of Oil, but the phase difference is not indicative of Oil (i.e., it is ambiguous result) (e.g., possibly indicative of a combination of Water and Gas), this information is not saved to the reference FIFO 407 when the amplifier 405 is present in the reference transducer and this information is not saved into the correlate FIFO 410 when the amplifier 405 is present in the correlation transducer. In an exemplary embodiment, when the phase difference is 90 degrees and the output voltage of the amplifier 405 is the voltage indicative of Gas (e.g., 0 volts), it can be concluded that the medium is in fact Gas. However, if the phase difference is less than 90 degrees and the output voltage of the amplifier 405 is indicative of Gas, it can be concluded that the medium is in fact a combination of Oil and Water. In an exemplary embodiment, when the output of the amplifier 405 is indicative of Gas, but the phase difference is not indicative of Gas (i.e., it is ambiguous result) (e.g., possibly indicative of a combination of Water and Oil), this information is not saved to the reference FIFO 407 when the amplifier 405 is present in the reference transducer and this information is not saved into the correlate FIFO 410 when the amplifier 405 is present in the correlation transducer.

Thus, while the flowmeter is performing a series of samples during a given period, and one of these samples is ambiguous (e.g., ambiguous for Gas or Oil), the corresponding counter for (e.g., Gas or Oil) is not incremented for that one sample. Thus, this sample data is essentially filtered out from flow rate calculations. Further, this allows the flow rate to be calculated for each phase (e.g., just Oil, just Water, just Gas), in addition to the flow rate for the entire medium, which could be done without filtering.

In an exemplary embodiment, the closer the phase difference is to 0, the more Water there is in the sample. Thus, a phase difference between 0 degrees and a value less than 90 degrees can be used to determine a Water to Gas ratio or Water to Oil ratio, for a given sample.

A phase difference less than 90 degrees may indicate there is a resistive component to the medium/material, which is possible if it includes Water, which contains salts causing a resistive factor, resulting in an electrical phase angle of the amplifier 405 output to shift towards 0 degrees. A 90 degree phase difference could mean that the zero crossover of the output of the amplifier 405 occurs ¼ of the period of an oscillator frequency of the oscillator 402 before the zero crossover of the oscillator signal itself.

The sensor 403 corresponds to a portion of the Dielectric Multiphase transducer of FIG. 2. For example, in FIG. 4, the sensor 403 is depicted as a capacitor having a left plate and a right plate, where the left plate is the first Rod 209 and the right plate is the second Rod 210. In an embodiment, the oscillator 402 is a high frequency sinusoidal oscillator that applies a voltage to the first Rod 209 to form the left plate of the capacitor. The other Rod 210 of the Transducer feeds the input of the Amplifier 405 (e.g., an operational amplifier) through a small capacitor Cs. In an embodiment, the capacitance of the capacitor Cs is chosen as the square root of the product of the Gas filled Transducer and its capacitance when filled with Water. This will increase the effective dynamic range of sensing, since the dielectric constant of Water is much higher than Oil or Gas.

The output voltage of the amplifier 405 is proportional in amplitude to the current flowing through the Sensor 403 at any time, and whose phase shift is related to the electrical impedance angle of the material "seen" by the Sensor 403, most sensitively in the apex of the "V" space between the Rods 209 and 210. Thus, the output voltage is a complete description of what Phase is in the Transducer at any time. The frequency of the oscillator 402 is selected to make the range of impedances seen by the Sensor 403 practical, typically from 1000 to 100,000 ohms. As a design option, the amplitude of the oscillator 402 can be automatically controlled to maintain, for example, a fixed Amplifier output voltage, which would then make the Oscillator voltage proportional to Sensor impedance, in that case.

The Transducer oscillator is also used as the reference in a Transducer signal amplifier Zero Crossover Detector within the Phase Comparator 404, providing a high-resolution measurement of the phase shift of the Amplifier 405 output to determine the phase of the mixture's impedance seen by the Sensor 403. As described previously, this is necessary to differentiate an Oil Signature from a false Water-Gas mixture from simulating an Oil signature by detecting the phase shift caused by the resistive component of contaminated Water.

The recorded time sequence of the random variations of the digitized amplifier 405 output is now the historical record of the instantaneous impedance of the Mixture as it flows past the Sensor 403. In an exemplary embodiment, the output of the amplifier 405 is an amplitude modulated RF signal. It is therefore convenient to Demodulate this RF signal in a Peak Detector 406 to produce a lower frequency signal which can be readily sequentially Digitized as commanded by the Registration pulse and fed into a FIFO 407. This data is the record of the sequence and residence duration of each individual Medium phase as it passes through the Multiphase Transducer. Integration of the relative time each phase's Signature was sensed represents the relative volume of each Phase, and depending on the selected integration period, either from the "beginning of time" or over a selected short time interval, can reveal fast or slow developing changes in the Well's performance.

Thus, the present and historical performance of each Wellhead can be readily determined in real time, and without the need to physically separate the Medium's phases.

Using the FIFO 407 to store the constantly varying value of Phase Signatures at the Reference site not only permits determination of the varying ratio of medium components, but also permits its use as a Reference for detection of the "same" Signature sequence as it arrives at the Correlation site a short time later. Computation of Flow Rate is then possible by dividing the known distance between Reference and Correlation sites by the time delay between generating a Reference Signature sequence, and detecting the same sequence by correlating the Signatures as they arrive at the Correlation site. For example, the correlation Transducer may stores samples (output voltages of its amplifier or values indicating Oil, Gas, or Water) in the Correlate FIFO 410 similar to those stored in the Reference FIFO 407 by the Reference Transducer, and the Correlator 408 can perform an a correlation on values (e.g., a first pattern) in the Correlate FIFI 410 and values (e.g., a second pattern) in the Reference FIFO 407 to determine a flow rate. For example, if the correlation indicates the first and second patterns are the same as similar enough (e.g., within a certain similarity), a flow rate can be calculated based on the distance between the transducers and the time it took for the first pattern to reach the Correlation transducer.

The very randomness of the sequence of Signatures is beneficial so long as minimal Phase mixing develops as the medium flows between Reference and Correlation sites. The flow straightener 501 shown in FIG. 5 will minimize Phase mixing. In an embodiment, the flow straightener 501 is implemented by a hollow tube. The angled faces of the rods 209 and 210 are inserted into a through-hole of the flow Straightener 501, and the medium flows through the flow Straightener 501 and over the angled faces of the rods 209 and 210.

Figure 5:
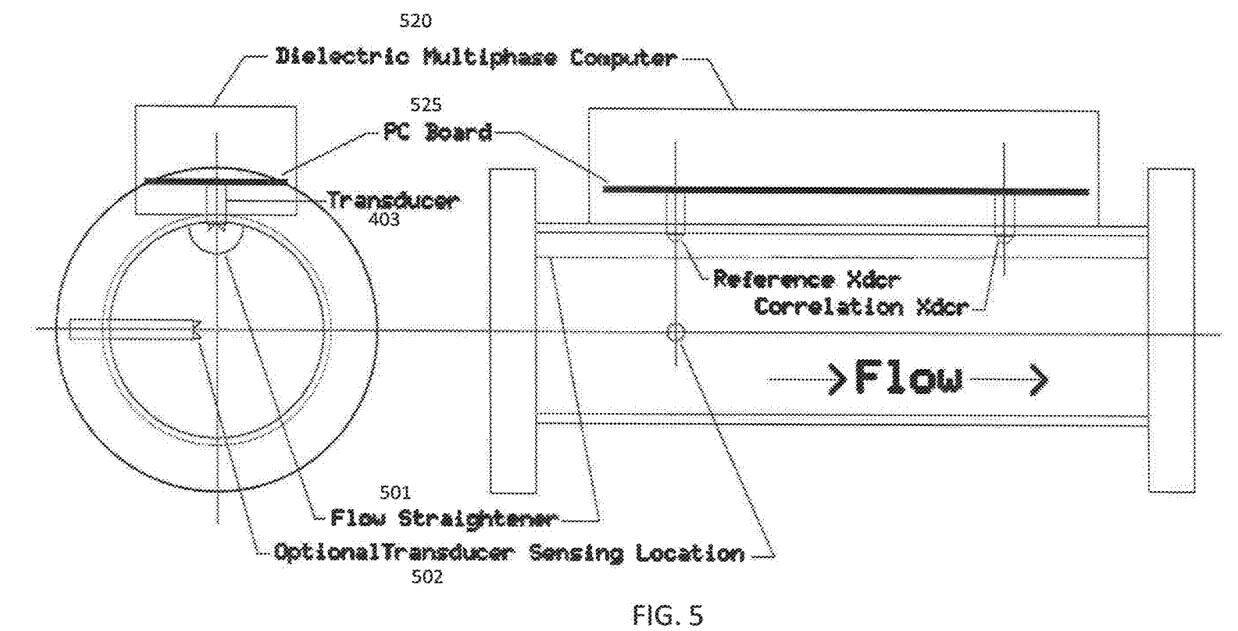
FIG. 5 illustrates the flowmeter installed on a spool according to an exemplary embodiment of the inventive concept.

Although the described embodiment may be preferred, it is also possible to produce longer Transducers which reach into alternative sensing regions within the flow stream, to produce data descriptive of local conditions within the flow stream, such as in 502 of FIG. 5.

Referring again to FIG. 4, the clock signal generator 401 drives the oscillator 402 (e.g., a Sine Wave generator). The clock driven oscillator 402 delivers its output to the input of the Oscillator Rod 209, and the Sensor Rod 210 is connected to the input of the Amplifier 405. The amplitude of the input current to the Amplifier 405 is inversely proportional to the electrical impedance of a dielectric constant Ks, based on the components in the field of the two Rods 209 and 210, and is therefore proportional to the value of the effective dielectric constant seen by the Capacitor formed by the Rods 209 and 210. Accordingly, the voltage output of the amplifier 405 is proportional to the medium's effective dielectric constant (or inversely proportional to its net impedance). Thus, by sensing the value of the output Voltage, in a Peak Detector 406, it is possible to control the amplitude of the Oscillator 402 (e.g., a Sine Wave Generator) to be proportional to the Sensor 403 impedance, and the phase shift between the Oscillator 402 and the output of the amplifier 405 represents the phase angle of the Medium's impedance.

Thus, in the case where the amplitude of the Oscillator 402 is controlled by feedback, it may be seen that the output amplitude of the oscillator 402 (e.g., Sine Wave Generator) as seen by a Peak Detector 406, is then inversely proportional to the current value of Ks, the current effective dielectric constant of the mixture of components within the field of the Transducer, or directly proportional to Zs, its impedance. Computation of the ratio of components will utilize mathematical computation of the effect of each component on Ks, and also historical and empirical data, as shown in FIG. 1A, as well as data on the time variability of the data stream amplitude and phase.

A Multiphase Dielectric Flowmeter Spool, containing the Transducers for determination of the relative percentage of Oil, Gas and Water in the flowing Medium will be installed at the wellhead downstream from the point where it emerges from the ground, and may include an integrated or remote Multiphase Flow Computer 520 (may also be referred to as a controller). In light of the analysis above, the spool can be installed vertically or horizontally. For example, a section of pipe in a pipeline transporting Oil or Gas may be removed, and the spool can be inserted into the removed space. The spool may include a flange on opposing ends so that each flange of the spool may be affixed to each end of the pipe. Any location that permits uniform distribution of the flow Medium contents is preferred. Mixing to permit this objective to be is not objectionable, so long as it does not reduce the size of the phase bubbles, as would be the case in an emulsification. However, if Flow Rate measurement is desired as well as determination of relative Phase content, the Spool may contain optionally include a Flow Straightener 501 to confine the flow contents in the region where the Reference and Correlation Transducers are mounted, as shown in FIG. 5 (e.g., Reference Xdcr is a Reference transducer like that of sensor 403 and Correlation Xdcr is Correlation transducer like that of sensor 403).

The Spool, shown in FIG. 5 exemplarily shows both Reference and Correlation Multiphase Dielectric Transducer installed, each within a typical Flow Straightener 501, and located, depending on installation conditions, where the flow Medium is deemed representative of the average Medium's phase distribution. If the distribution is suspected of not being uniform, as many Transducers as deemed needed to provide a True Average may be installed, each requiring its own Sensing Circuit if Multiplexing is not employed, the results of each to be averaged computationally. An optional mounting location, showing a sensing location near the center of the Spool is shown as an exemplary option demonstrating the flexibility of this Transducer design concept.

An Integrated Spool mounted Multiphase Dielectric Computer 520, shown FIG. 5, permits direct Sensor connections to a Printed Circuit Board 525, eliminates the need for external cable connections, other than an external power input, and data output if not provided wirelessly. In an exemplary embodiment, the Rods of each dielectric transducer (e.g., 209 and 210 or 609 and 610) are inserted directly into pads, sockets, or connectors of the Printed Circuit Board 525. For example, a first end of reference Rod 209 of a reference transducer is inserted in an interior of the spool and the second opposing end of the reference Rod 209 contacts a first one of the pads, a first end of a reference Rod 210 of the reference transducer is inserted in an interior of the spool and the second opposing end of the reference Rod 210 contacts a second one of the pads, a first end of a correlation Rod 209 of a correlation transducer is inserted in an interior of the spool and the second opposing end of the correlation Rod 209 contacts a third one of the pads, a first end of a correlation Rod 210 of the correlation transducer is inserted in an interior of the spool and the second opposing end of the correlation Rod 210 contacts a fourth one of the pads. Otherwise a Remote Multiphase Dielectric Computer may be connected via coaxial cables from the Transducer. In the case where multiple Transducers are utilized, secondary Transducers may be connected to an Integral computer via small metal tubing which exits from the holes shown on the sides of the Transducer.

Figure 6:
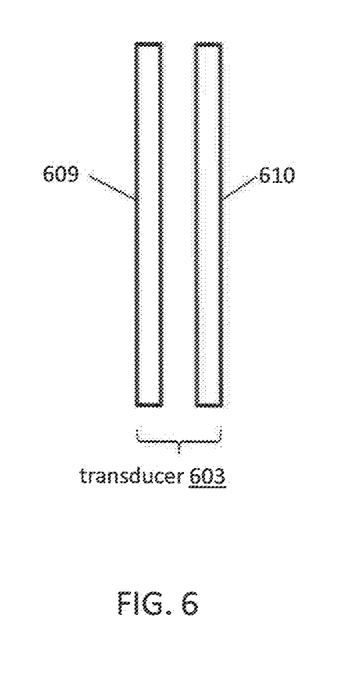
FIG. 6 illustrates a multiphase dielectric transducer according to an exemplary embodiment of the inventive concept.

While FIG. 2 shows a Transducer with a first and second rods 209 and 210 having particular shape, embodiments of the inventive concept are not limited thereto. For example, FIG. 6 shows a Transducer 601 according to an alternate embodiment where the rods include a first Rod 609 (e.g., a conductive material such as stainless steel) and a second Rod 610 (e.g., a conductive material such as stainless steel) spaced apart from one another. In this embodiment, the Rods 609 and 610 are parallel to one another, but the inventive concept is not limited thereto. For example, the Rods 609 and 610 may be positioned with an acute angle or an obtuse angle therebetween. Thus, the sensor 403 in FIG. 4 may be replaced with Transducer 601. For example, the left plate of sensor 403 may be replaced with Rod 609 and the right plate of sensor 403 may be replaced with Rod 610. For example, the transducer 403 shown in FIG. 5 as being a Transducer including Rods 209 and 210, the ground sheet 206, and insulators 207, may be replaced with Rods 609 and 610. Further, while Rods 609 and 610 are illustrated in FIG. 6 has being rectangular (e.g., a 3D rectangle), it can have other shapes in alternate embodiments such as cylindrical.

Although the illustrative embodiments have been described herein with reference to the accompanying drawings, it is to be understood that the present invention is not limited to those precise embodiments, and that various other changes and modifications may be affected therein by one of ordinary skill in the related art without departing from the scope or spirit of the invention. All such changes and modifications are intended to be included within the scope of the disclosure.

What is claimed is:

1. A sensor for detecting relative amounts of components within a mixture, the sensor comprising:
   a dielectric transducer comprising a first conductive rod and a second conductive rod;
   an oscillator configured to apply a voltage to the first conductive rod;
   an amplifier configured receive a voltage from the second conductive rod as an input; and
   a controller configured to periodically sample an output voltage of the amplifier to generate a plurality of sample voltages, compare the sample voltages against distinct voltage values for identifying each of the components to determine the relative amounts of the components,
   wherein the first conductive rod includes a first angled front side disposed at a first acute angle relative to a first back side of the first conductive rod, the second conductive rod includes a second angled front side disposed at a second angle relative to a second back side of the second conductive rod, the first and second angled front sides face each other, and the mixture flows through a space between the first and second front angled sides.

2. The sensor of claim 1, wherein the controller determines the relative amounts of the components by integrating the relative amount of time each component was identified.

3. The sensor of claim 1, wherein the first conductive rod includes a first portion below the first angled side and a second portion below the second angled side, and the dielectric transducer includes a three-layer region between the first and second portions, the three-layer region including a first insulator covering a first side of the first portion, a second insulator covering a second side of the second portion, and a conductive sheet between the insulators that is grounded.

4. The sensor of claim 3, wherein the first and second sides are flat and the back sides are semi-conical.

5. The sensor of claim 1, wherein the amplifier is designed so that its output voltage is a first voltage value among the distinct voltage values to indicate oil, a second voltage value among the distinct voltage values to indicate gas, and a third voltage value among the distinct voltage values to indicate water.

6. The sensor of claim 1, further comprising a phase comparator configured to operate on the voltage applied by the oscillator and the output voltage of the amplifier to determine a phase difference, wherein the controller uses both the output voltage and the phase difference to determine a given one of the components of the mixture.

7. The sensor of claim 6, wherein the controller determines the given one component is oil when the output voltage is a first voltage value among the distinct voltage values and the phase difference is 90 degrees and the controller determines the given one component is a mixture of water and gas when the output voltage is the first voltage value and the phase difference is less than 90 degrees.

8. The sensor of claim 7, wherein the controller determines the given one component is gas when the output voltage is a second voltage value among the distinct voltage values and the phase difference is less than 90 degrees and the controller determines the given one component is a mixture of water and oil when the output voltage is the second voltage value and the phase difference is less than 90 degrees.

9. The sensor of claim 8, wherein the controller determines the given one component is water when the output voltage is a third voltage value among the distinct voltage values.

10. The sensor of claim 1, further comprising a variable capacitor connected to the input of the amplifier, wherein the voltage applied by the oscillator to the first conductive rod has a positive polarity, and the oscillator applies the voltage of a negative polarity to the variable capacitor.

11. A dielectric flowmeter comprising:
   a first dielectric transducer comprising a first pair of conductive rods, a first oscillator configured to apply a first voltage to a first conductive rod of the first pair, a first amplifier configured receive a voltage from a second conductive rod of the first pair as an input;
   a second dielectric transducer comprising a second pair of conductive rods, a second oscillator configured to apply a second voltage to a first conductive rod of the second pair, a second amplifier configured receive a voltage from a second conductive rod of the second pair as an input; and
   a controller configured to determine a flow rate from an output of the first amplifier and an output of the second amplifier,
   wherein each of the first conductive rods includes a first angled front side disposed at a first acute angle relative to a first back side of the corresponding first conductive rod, each of the second conductive rods includes a second angled front side disposed at a second angle relative to a second back side of the corresponding second rod, the first and second angled sides of the first pair of conductive rods face each other across a first space, the first and second angled sides of the second pair of conductive rods face each other across a second space, and the mixture flows through the first space and the second space.

12. The flowmeter of claim 11, further comprising a spool, wherein the first pair of conductive rods are inserted into an interior of the spool at a first position, and the second pair of conductive rods are inserted into the interior at a second position.

13. The flowmeter of claim 12, wherein the spool includes a hollow tube, and each of the conductive rods are inserted into the tube.

14. The flowmeter of claim 11, where each pair of conductive rods includes a three-layer region between the corresponding first and second conductive rods, the three-layer region including a first insulator covering a first side of one of the corresponding first and second conductive rods, a second insulator covering a second side of the other one of the corresponding first and second conductive rods, and a conductive sheet between the first and second insulators that is grounded.

15. The flowmeter of claim 11, wherein each amplifier is designed so that its output voltage is a first voltage value to indicate oil, a second voltage value to indicate gas, and a third voltage value to indicate water, wherein the first, second, and third voltage values differ from one another.

16. The flowmeter of claim 12, wherein the first dielectric transducer includes a first buffer storing first values generated from outputs of the first amplifier, and the second dielectric transducer includes a second buffer storing second values generated from outputs of the second amplifier.

17. The flowmeter of claim 16, wherein the controller generates a first pattern from the first values, generates a second pattern from the second values, and determines the flow rate when the first pattern is similar to the second pattern by subtracting a time the second pattern is detected from a time the first pattern is detected to generate a travel time and dividing a distance between the first and second positions by the travel time.

18. The flowmeter of claim 12,
wherein the first dielectric transducer filters out outputs of the first amplifier having a certain phase difference with the first voltage,
wherein the second dielectric transducer filters out outputs of the second amplifier having the certain phase difference with the second voltage, and
wherein the controller determines the flow rate from the remaining outputs of the first amplifier and from the remaining outputs of the second amplifier.

* * * * *